United States Patent [19]

Höhl et al.

[11] 4,395,491

[45] Jul. 26, 1983

[54] METHOD FOR ISOLATING SOLID MATTER FROM A SALINOMYCIN CULTURE BROTH

[75] Inventors: Rolf Höhl, Hofheim; Helmut Heine, Kronberg, both of Fed. Rep. of Germany

[73] Assignee: Hoechst Aktiengesellschaft, Frankfurt am Main, Fed. Rep. of Germany

[21] Appl. No.: 234,318

[22] Filed: Feb. 13, 1981

[30] Foreign Application Priority Data

Feb. 15, 1980 [DE] Fed. Rep. of Germany ....... 3005642

[51] Int. Cl.³ .............................................. C07G 17/00
[52] U.S. Cl. ................................... 435/262; 435/267; 435/887
[58] Field of Search .............. 435/248, 887, 261, 253, 435/262, 267; 424/122, 121, 123, 283; 426/271, 61, 807

[56] References Cited

U.S. PATENT DOCUMENTS

| | | | |
|---|---|---|---|
| 2,710,810 | 7/1955 | Strashun | 426/471 X |
| 3,103,439 | 10/1963 | Williams | 426/471 X |
| 3,600,818 | 8/1971 | Lang et al. | 426/471 X |
| 3,716,579 | 2/1973 | Knauseder et al. | 260/488 B |
| 3,819,836 | 6/1974 | Shu et al. | 424/124 |
| 3,832,462 | 8/1974 | Shu et al. | 424/123 |

FOREIGN PATENT DOCUMENTS

| | | |
|---|---|---|
| 3644 | 8/1979 | European Pat. Off. . |
| 2035814 | 2/1971 | Fed. Rep. of Germany . |
| 2154633 | 5/1972 | Fed. Rep. of Germany . |
| 251112 | 10/1947 | Switzerland . |
| 1378414 | 12/1974 | United Kingdom . |

OTHER PUBLICATIONS

Kinoshi et al., "The Structure of Salinomycin, A New Member of Polyether Antibiotics", Tetrahedron Letters, vol. 49, pp. 4955–4958, (1973).

Rose et al., "The Condensed Chemical Dictionary", 7th Edition, p. 162, (1970).

Chem. Abst. 90, 150298a, (1979).

*Primary Examiner*—R. B. Penland
*Attorney, Agent, or Firm*—Curtis, Morris & Safford

[57] ABSTRACT

What are disclosed are a method for recovering solid matter from a salinomycin culture broth by spray drying a low-fat culture broth in the presence of a physiologically acceptable solid agent preventing agglomeration, and a solid product so prepared.

4 Claims, No Drawings

METHOD FOR ISOLATING SOLID MATTER FROM A SALINOMYCIN CULTURE BROTH

It is known that salinomycin as a fodder additive has a very favorable influence on growth and fodder utilization, especially in ruminants and pigs. It is also used as a coccidiostatic agent in veterinary medicine.

The isolation of the active substance from the fermentation broth is very complicated and expensive, since numerous stages have to be gone through, for example lyophilization or extraction, which involve high investment, material and energy expenses.

For the use of salinomycin as fodder additive it is not necessary, however, to prepare the active substance in its pure form. For the said purpose it may be obtained together with the solids from the salinomycin culture broth and may be employed in this form. The product thus obtained is marked by considerably lower costs of production.

When attempts were made to use spray drying (which can easily be carried out in comparable cases) to isolate solid matter from the culture broth, unexpected difficulties were encountered since the solids agglomerated, forming lumps which could not be further processed. The agglomerates and lumps formed are evidently caused by the material properties of salinomycin and also by fats and fat-like products contained in the solids which show these undesirable properties at the high temperatures, the conditions of humidity and, the mechanical stress which are unavoidable when using the process.

It has now been found that the solid matter may be isolated from the salinomycin culture broth without agglomeration by obtaining the lowest possible content of extractable fats and fat-like substances in the fermentation process and adding a physiologically acceptable finely powdered material, designated as an anti-agglomeration agent, during spray drying.

The individual stages of the process of the invention may be described for example as follows.

The fermentative preparation of salinomycin is carried out in known manner [cf. Y. Miazaki et al., J. Antibiotics 27, pages 814 to 821 (1974); H. Kinashi et al., Tetrahedron Letters 49, pages 4955 to 4958 (1973) and H. Kinashi et al., Agr. Biol. Chem. 40, pages 1625 to 1632 (1976)], wherein mainly fats of different origin, such as soy bean oil, sesame oil, colza oil, safflower oil, olive oil, codliver oil, methyl oleate, methyl myristate and methyl linoleate are used as a carbon source and as defoaming agents.

The fermentation is carried out until, at the point of harvesting, the amount of these fats, or of fat-like products formed therefrom by degradation, such as lauric acid, myristic acid, palmitic acid, stearic acid, arachnoic acid, oleic acid, linolic acid and palmitoleic acid, which may be extracted with water-immiscible organic solvents, for example methylene chloride, gasoline, benzene, chloroform, carbon disulfide, carbon tetrachloride, tetralin or trichloroethylene, together with salinomycin, the usual and determined in common manner [cf. e.g. Römpp Chemie Lexikon, 7th edition, 2nd volume, page 1072, catchword "Extraktion"; Deutsche Lebensmittel-Rundschau 69, 470–472 (1973)], is at the lowest possible level, preferably less than about 2% of the culture broth, the salinomycin content not being included any more in this value. The attainment of this value is checked by constant sampling.

In order to render the spray drying more economical, the culture broth can be preconcentrated in an evaporator in known manner, for example from a solids content of from about 13 to 20% to a content of from about 30 to 50%, preferably about 40%. The scope of preconcentration is determined by the ability of the product to be pumped. It is required that transport and atomization are still easily possible.

The spray drying is carried out in known manner in a drying tower (cylindrical tower with conical outlet), such as a disk atomizer or a nozzle drier. For example, a disk atomizing tower having a diameter of 2.2 m with a cylinder length of 1.2 m and an attached cone of 60°, or a nozzle atomizing tower having a diameter of 1.6 m, a cylinder length of 4 m and a cone of 60°, may be used.

The inlet temperature of the air may be between about 140° and 220° C., preferably from about 190° to 210° C., and the outlet temperature between about 80° and 100° C., preferably from about 85° to 95° C.

An optimum drying result is obtained if the relative humidity of the air at the outlet of the drying tower is in the range of from about 8 to 20%, preferably from about 10 to 15%.

In the presence of ignition sources, a gas current having an oxygen content which has been reduced as compared with the normal content and is for example from about 8 to 15%, preferably less than about 14%, may be employed in order to avoid dust explosions.

As an anti-agglomeration agent added according to the invention, any physiologically acceptable finely powdered material may be used which is suitable to suppress the plastic properties of the solid matter from the culture broth—probably by a diluting and covering effect on the spray-dried particles—to an extent that lump formation and agglomeration, which take place especially under the required temperature and pressure conditions are, no longer to be observed.

There may be mentioned preferably finely divided calcium carbonates and silicic acids of natural or synthetic origin, such as chalk, precipitated silicic acid, diatomaceous earth, also talc and kaolin, the anti-agglomeration agents optionally being employed by themselves or in the form of mixtures with one another. According to the invention, an addition of kieselguhr (for example Diamol GM ®) has proved to be advantageous.

The anti-agglomeration agent may be added, for example, by introducing it via a metering device (for example a metering screw, a vibration groove or a metering belt) from above into the drier, together with the main air current being introduced in the usual manner in a parallel current with the culture broth, but preferably with a secondary air current being directed in a way that the particles of anti-agglomeration agent strike those portions of the culture broth solids which have already been largely dried. The dosing is effected by free fall or by means of a suitable atomizer, for example a two-component nozzle, at one or several, preferably three, places. In the case of a nozzle atomizing tower, the secondary air current is directed preferably almost vertically to the drier air. In principle, the process of the invention may also be carried out with a drier operating in countercurrent.

Depending on the respective product properties (agglomeration especially under strain of pressure and temperature), for example from about 1 to 25%, preferably from about 4 to 10% (calculated on an employed culture broth containing generally from about 10 to 15% of solid matter), of anti-agglomeration agent may be constantly added over the total drying period. The type of anti-agglomeration agent may also influence the amount added. For example, when using aerosil, an amount of from about 1 to 2% may already be sufficient, and when using kieselguhr, from about 4 to 5%, in order to obtain a spray-dried solid substance which contains from about 15 to 25% of salinomycin.

The amount of anti-agglomeration agent may also readily be increased to a value of far more than 25%, however, this does not generally involve any considerable improvement of the product.

If in the fermentation the above-mentioned low values of extractable fats or fat-like products—which should not exceed 3%, if possible, and should preferably be below about 2%—cannot be reached at all or only with difficulty, the culture broth thus showing a particularly strong tendency to agglomeration, it may be suitable to introduce at least part of the total amount of anti-agglomeration agent into the culture broth with stirring already at any point before the spray drying. Thus, for example, an amount of from about 2 to 10%, preferably from about 4 to 5% (calculated on the culture broth), can be added with agitation, in which case the value of 10% may also readily be exceeded. The addition is carried out by means of appropriate introducing elements.

The dried solid matter is discharged in known manner, for example via a pneumatic transfer tube and pneumatic removal by suction.

In order to obtain a material as homogeneous as possible for introduction into the drying tower, it may be suitable, prior to spray drying, to comminute. Such agglomerates may sometimes be found after the addition of inert material or with culture broths that have not been freshly fermented. Comminution may be carried out in a known manner, for example by wet grinding with colloid mills.

The result of the process of the invention was surprising and could not have been foreseen after the failure of numerous preliminary attempts to eliminate lump formation, which severely hindered the isolation of the solids, by simply strongly reducing the content of fats or fat-containing substances during fermentation or by adding the anti-agglomeration agent to the culture broth only. Because of the measures of the invention it has become possible for the first time to obtain a product excellently suitable as a fodder additive in a simple manner and with low costs of production.

The composition of the dried solids obtained according to the invention from the salinomycin culture broth may vary within determined limits depending on the composition of the culture broth. As a rule the salinomycin-containing solid matter obtained according to the invention is apt to show a content of anti-agglomeration agent of from about 5 to 60%, preferably from about 8 to 25%, and a slinomycin content of from about 15 to 30%, preferably from about 18 to 25%.

The following Examples illustrate the invention.

EXAMPLE 1

After a fermentation with a complete fat degradation, a culture broth having a solids content of 20% was obtained. The microorganism was killed by adding 1.0% of formalin (35% aqueous solution), calculated on the culture broth, and the pH value of the culture broth was adjusted to 9.5 with 30% sodium hydroxide solution.

The culture broth was fed into the disk atomizing drier having a diameter of 2.2 m, a cylinder length of 1 m, an attached cone of 60° and a disk of a diameter of 120 mm by means of an accentric spiral pump with 24,000 rpm.

The inlet temperature of the drier was 200° C. 1,200 Kilograms of drying gas were introduced per hour with an oxygen content of less than 14%. With a supply of 85 kg of culture broth per hour, the drier outlet temperature was 85° C.

5% of kieselguhr, calculated on the culture broth, were introduced in doses into the tower by free fall via a metering screw and a funnel. The material was discharged from the cyclones through vortex tubes.

In this manner, 95% of the employed solid matter from the culture broth were obtained in the form of a free-flowing material. The production strain could no longer be detected in the product.

EXAMPLE 2

After a fermentation with a fat degradation which was not quite complete (3.5% of residual fat), the microorganisms of the culture broth which contained 18% of solid matter were killed by adding 1% of formalin (35% aqueous formalin solution), calculated on the culture broth, and the pH of the culture broth was adjusted to 10 with 30% sodium hydroxide solution.

In order to improve the ability of the product, which showed a strong tendency to agglomeration and lump formation, to be pumped and sprayed, 5% of kieselguhr culture broth, and lumps that were already present were comminuted prior to spray drying by means of a colloid mill.

The material thus prepared was introduced into a two-component nozzle drier with the aid of an accentric spiral pump. The drier had a diameter of 1.2 m, a length of the cylinder of 4 m and was provided with an attached cone of 60°.

The inlet temperature in the drier was 200° C. 900 Kilograms of drying gas were fed in per hour with an oxygen concentration of less than 14%. With a supply of 45 kg of culture broth per hour, the drier outlet temperature was 85° C.

By means of a metering screw, 5% of kieselguhr (Diamol GM ®) were introduced into the drying tower likewise via a two-component nozzle vertically to the drying gas current.

In this manner, 92% of the employed solid matter from the culture broth were obtained in the form of a free-flowing product. Attempts to isolate the production strain from the spray powder were unsuccessful.

EXAMPLE 3

A culture broth as indicated in Example 1 was concentrated in a thin-film evaporator prior to being introduced into the drying tower. Thereafter the solids mass was 40%. The drying was carried out as has been described in Example 1.

EXAMPLE 4

A culture broth as indicated in Example 2 was dried in the manner described therein, while using 15% of chalk (calculated on the culture broth) as the anti-agglomeration agent, instead of kieselguhr. Of these, 5% were introduced with agitation into the culture broth, and 10% were added to the drying gas.

What is claimed is:

1. A method for isolating the solid matter from a broth in which salinomycin has been produced by fermentation, which method consisting essentially of fermenting said broth to reduce its content of fats and fat-like substances to a value of less than 2 percent, which fats and fat-like substances are present in said broth as a carbon source and defoaming agent, and spray drying said broth while adding thereto a physiologically acceptable finely powdered material as an anti-agglomeration agent in a manner so that the particles of said anti-agglomeration agent strike those portions of the culture broth solids which have already been largely dried, said anti-agglomeration agent being present in an amount sufficient to suppress agglomeration of said solid matter.

2. A method as in claim 1 wherein said finely powdered material is calcium carbonate or silicic acid.

3. A method as in claim 1 wherein said broth has a solids content between about 13 and 20 percent prior to spray drying.

4. A method as in claim 1 wherein said broth is concentrated to a solids content between about 30 and 50 percent prior to spray drying.

* * * * *